United States Patent [19]

Shorr et al.

[11] Patent Number: 5,264,555
[45] Date of Patent: Nov. 23, 1993

[54] PROCESS FOR HEMOGLOBIN EXTRACTION AND PURIFICATION

[75] Inventors: Robert G. L. Shorr, Edison; Kwang Nho, Somerset; Myung-ok P. Cho, Highland Park; Chyi Lee, Princeton Junction; Barbara Czuba, Bridgewater; Hariharan Shankar, Edison, all of N.J.

[73] Assignee: Enzon, Inc., South Plainfield, N.J.

[21] Appl. No.: 913,138

[22] Filed: Jul. 14, 1992

[51] Int. Cl.$^5$ .......................... C07K 3/02; C07K 3/12; C07K 3/22; C07K 15/06
[52] U.S. Cl. .................................... 530/385; 530/416; 530/423; 530/427
[58] Field of Search ............... 435/70.4; 530/416, 423, 530/427, 385; 514/6

[56] References Cited

U.S. PATENT DOCUMENTS

| | | | |
|---|---|---|---|
| 4,001,200 | 1/1977 | Bonsen et al. | 530/385 |
| 4,001,401 | 1/1977 | Bonsen et al. | 530/385 |
| 4,053,590 | 10/1977 | Bosen et al. | 530/385 |
| 4,336,248 | 6/1982 | Bonhard et al. | 530/385 |
| 4,412,989 | 11/1983 | Iwashita et al. | 530/385 |
| 4,529,719 | 7/1985 | Tye | 514/6 |
| 4,584,130 | 4/1986 | Bucci et al. | 530/385 |
| 4,670,417 | 6/1987 | Iwasaki et al. | 514/6 |
| 4,764,279 | 8/1988 | Tayot et al. | 530/385 |
| 4,777,244 | 11/1988 | Bonhard et al. | 530/385 |
| 4,900,780 | 2/1990 | Cerny | 525/54.1 |
| 5,084,558 | 1/1992 | Rausch et al. | 530/385 |
| 5,115,100 | 5/1992 | Wu et al. | 530/385 |

FOREIGN PATENT DOCUMENTS 9615 7/1991 World Int. Prop. O. .

OTHER PUBLICATIONS

Rabiner et al., *J. Exp. Med.*, 126, 1127 (1967).
DeVenuto et al., *J. Lab. Clin. Med.*, 89, 509 (1977).
Bolin et al., "Advances In Blood Substitute Research", *Prog. Clin. Biol. Res.*, 122, 117 (1983).
Litwin et al., *An. Surg.*, 157(4), 485 (1963).
White et al., *J. Lab. Clin. Med.*, 108(2), 121 (1986).
Simoni et al., *Anal. Chim. Acta.*, 249, 169 (1991).
Hedlund et al., "Advances In Blood Substitute Research", *Prog. Clin. Biol. Res.*, 122, 71 (1983).

*Primary Examiner*—Jeffrey E. Russel

[57] ABSTRACT

Methods are disclosed for separating hemoglobin from erythrocytes by contacting erythrocytes with a hypotonic buffer solution at a rate sufficient to render the release of hemoglobin from said erythrocytes without significant lysis. The hemoglobin is then separated from the erythrocytes. Methods are also disclosed for purifying hemoglobin solutions of DNA, endotoxins and phospholipids by contacting the hemoglobin solutions with an anion exchange medium.

64 Claims, No Drawings

PROCESS FOR HEMOGLOBIN EXTRACTION AND PURIFICATION

BACKGROUND OF THE INVENTION

The present invention relates to methods for extracting hemoglobin from erythrocytes and purifying hemoglobins. The methods of the present invention are particularly suitable for the extraction and purification of hemoglobin from erythrocytes on a commercial scale.

Advances have occurred in recent years in the development of hemoglobin-based blood substitutes. Such transfusional fluids serve as alternatives to whole blood or blood fractions for use as oxygen carriers and plasma expanders.

The use of whole blood and fractions thereof has grown increasingly disfavored because of the risk of immune or non-immune reactions and infections, such as acquired immunodeficiency syndrome. Even if it were possible to reduce these risks to an acceptable level, a need would still exist for non-native hemoglobin-based blood substitutes because of the chronic short supply of human-based products. To meet the demand for transfusional fluids, researchers have sought to develop a hemoglobin-based blood substitute free of the risks associated with whole blood and whole blood products.

Initial efforts were directed to developing hemoglobin solutions free of stromal components. Stromal components had been identified as a cause of coagulopathy and associated renal failure. Rabiner et al., *J. Exp. Med.*, 126, 1127 (1967), used centrifugation and ultrafiltration procedures to prepare stroma-free hemoglobin solutions. Stroma-free hemoglobin solutions were prepared by re-crystallization by DeVenuto et al., *J. Lab. Clin. Med.*, 89, 509 (1977).

The need to remove stromal phospholipids from hemoglobin-based blood substitutes is well-known. See, e.g., Bolin et al., "Advances In Blood Substitute Research," *Prog. Clin. Biol. Res.*, 122, 117 (1983). In addition, hemoglobin-based blood substitutes must have a low oxygen affinity and a long transfusion half-life, and be substantially free of endotoxins, DNA and non-heme proteins and polypeptides.

Stromal contamination results from proteolysis during the separation of hemoglobin from erythrocytes. In PCT Patent Application No. WO 91US/09615, this problem was addressed by dialyzing the erythrocytes under slightly hypoosmotic conditions that rendered the cell membranes permeable to hemoglobin with a minimum of lysis. Nevertheless, unwieldy multiple chloroform extractions and centrifugations were still needed to reduce the stromal phospholipids to safe levels.

Endotoxins are found as a result of bacterial contamination. A synergistic toxicity between hemoglobin and endotoxin was recognized as early as 1963 by Litwin et al., *Ann. Surg.*, 157(4), 485 (1963). White et al., *J. Lab. Clin. Med.*, 108(2), 121 (1986) reported that stroma-free hemoglobin solutions purified to less than 0.12 EU/mL (120 picograms endotoxin per milliliter) produced cardiac rhythm disturbances and coagulation abnormalities. Heretofore, such endotoxin levels were ordinarily considered acceptable for pharmaceutical compositions for large volume parenteral administration.

U.S. Pat. No. 5,084,558 discloses the separation of phospholipids and endotoxins from hemoglobin solutions by High Performance Liquid Chromatography (HPLC) using a quaternary amine anion exchange medium on a silica support matrix. The three components are separated by an elution gradient, with release of the phospholipids taking place prior to the elution of the hemoglobin, and the endotoxins eluting after the hemoglobin. Simoni et al., in *Anal. Chim. Acta.*, 249, 169 (1991) attributed the residual toxicity of endotoxin and phospholipid purified hemoglobin solutions to non-heme peptides and other proteins, which are not separated by any single anion-exchange liquid chromatography medium. A commercially impractical purification method using a combination of different anion-exchange liquid chromatography columns was also suggested.

The purification methods disclosed to date have also failed to provide for the large-scale commercial extraction and purification of hemoglobin. HPLC procedures are limited by the size of available columns and flow rates that are normally measured in milliliters rather than liters per minute. See, e.g., Hedlund et al., "Advances in Blood Substitute Research," *Prog. Clin. Biol. Res.*, 122, 71 (1983). This is particularly true of affinity chromatography endotoxin separation techniques, which use chromatography columns containing 1 milliliter of separation media.

Thus, there remains a need for commercially feasible methods for the large-scale commercial extraction and purification of hemoglobin.

SUMMARY OF THE INVENTION

It has now been discovered that hemoglobin can be separated from erythrocytes by a simple process that can be readily adapted for large-scale commercial production. In particular, a hemoglobin solution is obtained by contacting erythrocytes with a hypotonic solution at a rate sufficient to render the release of hemoglobin from the erythrocytes without significant lysis. The hemoglobin is then separated from the erythrocytes.

Preferably, concentrated erythrocytes are diluted at a controlled rate with a hypotonic buffer solution until a specific concentration of hemoglobin in the buffer solution is obtained. The hypotonic buffer solution preferably has an osmolality between about 100 and about 350 milliosmoles/kg. In accordance with another aspect of the present invention, the step of separating a hypotonic hemoglobin solution from hemoglobin-permeable erythrocytes further includes the steps of microfiltering the hypotonic solution containing erythrocytes so that a hemoglobin microfiltrate in the hypotonic solution is obtained, and recovering the hemoglobin microfiltrate.

The present invention incorporates the discovery that a concentration range exists, within which a hypotonic buffer solution can be utilized to separate hemoglobin from erythrocytes without significantly lysing cell membranes. While phospholipid levels up to 0.15 weight percent and endotoxin contaminants may remain, these materials can be immediately removed by known processes. The resulting hemoglobin product can also be applied to end-uses in which such phospholipid or endotoxin levels are less critical. The hemoglobin product may also be utilized as an intermediate in the production of hemoglobin-based blood substitutes before being purified of any endotoxins and phospholipids.

It has also been discovered that hemoglobin-containing solutions having an osmolality between about 100 and about 250 milliosmoles/kg can be contacted with certain anion exchange media to selectively bind DNA, phospholipids or endotoxins present, but will not bind any hemoglobin. Accordingly, the hemoglobin solutions can be purified of any residual DNA, phospholipids and endotoxins. Significantly, the hemoglobin microfiltrate in the hypotonic solution resulting from the microfiltering step of the present invention is within this osmolality range. Accordingly, this discovery can be utilized to purify the microfiltrate of any DNA, endotoxins or residual phospholipids.

Included within this discovery is the realization that essentially any hemoglobin product, regardless of the method by which it is produced, can be purified of DNA, endotoxins and phospholipids by contacting solutions of the hemoglobin product having an osmolality between about 100 and about 250 milliosmoles/kg with the anion exchange media. Furthermore, solutions of hemoglobin-based blood substitutes can be purified of DNA, endotoxins and phospholipids by processes incorporating this discovery.

Therefore, in accordance with another aspect of the present invention, a method is provided for purifying a hemoglobin-containing solution of DNA, phospholipids and endotoxins, which method includes the steps of:

(a) providing a hemoglobin-containing solution having an osmolality between about 100 and about 250 milliosmoles/kg and a pH greater than about 7.0;

(b) contacting the solution with an anion exchange medium, wherein the anion exchange medium is capable of selectively binding DNA, phospholipids and endotoxins, but not hemoglobin, at the pH and osmolality of the solution, so that DNA, phospholipids and endotoxins bind to the medium and the hemoglobin remains in the solution; and (c) recovering the hemoglobin solution.

The contacting step is preferably performed by treating the hemoglobin solution with an anion exchange resin, such as in a liquid chromatography column. More preferably, the chromatography treating step is performed by conventional liquid chromatography techniques.

The combined hemoglobin separation and purification methods represent a significant improvement in efficiency over the prior art. A hypotonic solution within the disclosed pH and osmolality range can be utilized to separate hemoglobin from erythrocytes. The resulting hemoglobin solution can then be contacted with the specified anion exchange medium to purify the hemoglobin of residual phospholipids and contaminating DNA and endotoxins.

Other features of the invention will be pointed out in the following description and claims, which disclose, by way of example, the principles of the invention and the best modes which have been presently contemplated for carrying them out.

DETAILED DESCRIPTION OF THE PREFERRED EMBODIMENT

The inventive process can be used to separate and purify hemoglobin from any appropriate mammalian source, depending upon need. At present, the most commercially viable hemoglobins are human and ruminant hemoglobins, particularly bovine hemoglobin. Human hemoglobin can be obtained from whole human blood, either freshly drawn or from the outdated supply of blood banks. Human hemoglobin can also be obtained from placentas or packed erythrocytes obtained from human blood donor centers.

Ruminant hemoglobins such as bovine or sheep are also useful. Bovine hemoglobin can be obtained, for example, from slaughter houses or donor herds expressly kept for this purpose. The choice of animal source is not critical, but will instead be made on the basis of commercial demand. The products of the present invention also have veterinary end-uses. Therefore, various animal sources are appropriate for the methods of the present invention. The hemoglobin can also be produced by recombinant methods including the establishment of transgenic herds or cells. Such transgenic animals may express wild type human, variant human or mutated human hemoglobin. Mixtures of various hemoglobins are also contemplated.

The inventive method first includes contacting erythrocytes with a hypotonic solution to render the erythrocyte membranes permeable to hemoglobin without lysing. The erythrocytes may be provided by samples of whole blood from the various source described above, or by concentrated preparations of erythrocytes. The erythrocyte preparations preferably have a concentration of at least 50% (wt./vol.) and more preferably have a concentration of at least 75% (wt./vol.). Erythrocyte preparations having a concentration of at least 95% (wt./vol.) are most preferred. The cells are preferably suspended in isotonic saline. Concentrated erythrocyte preparations known to those of ordinary skill in the art as "packed red cells" are particularly suitable for use in the present invention. It is also preferred that the erythrocytes have a hemoglobin concentration of greater than or equal to 30 g/dL.

In an alternative aspect of the invention, concentrated erythrocyte preparations have been washed at least once with a sterile, pyrogen-free isotonic saline solution. "Wash" or "washed" is a term of art used by those of ordinary skill in the art in connection with erythrocyte concentrations. This refers to a rinsing of the cells by well-known techniques to remove plasma protein contaminants. Preferably, the erythrocyte concentrate has been washed more than once, so that the concentrate is substantially free of plasma proteins.

The concentrated erythrocytes are also preferably substantially free of leukocytes and reticulocytes. Reticulocytes represent a significant source of DNA contamination as well as some protein contamination.

The method of the present invention for the removal of endotoxins from hemoglobin solutions is highly effective. However, optimum results are obtained when precautions are observed to minimize endotoxin contamination. This would include utilizing conventional aseptic techniques throughout the processes of the invention. All equipment and materials should be "pyrogen-free" as that term is understood by those of ordinary skill in the art. More particularly, the concentrated erythrocytes should have an endotoxin level less than about 1.0 EU/mL; the buffer solutions should have an endotoxin level less than about 0.06 EU/mL; the anion exchange media should have an endotoxin level less than about 0.06 EU/mL; and all process water should have an endotoxin level less than about 0.03 EU/mL.

Endotoxin levels can be measured by the Limulus Amebocytic Lysate (LAL) assay. The endotoxin levels are established with reference to measurements made with gel clot assays or kinetic turbidometric assays. The appropriate type of assay to be used for a given material to be tested is well known. Containers, equipment and anion exchange media are rendered pyrogen free by rinsing or soaking in 0.1 to 1.0N NaOH followed by extensive rinsing with endotoxin-free water.

Erythrocytes having endotoxin levels less than about 1.0. EU/mL are obtained using aseptic techniques for blood collection, storage and concentration. Such aseptic techniques are well-known to those of ordinary skill in the art. An aseptic blood collection technique is disclosed in the above-cited U.S. Pat. No. 5,084,588. For example, large collection trochars are used to extract the blood in a sterile manner by careful insertion and handling. Particular care is taken not to puncture the animal's esophagus. The animal hide is washed, cut away, peeled back, and the trochar then inserted into a major vessel close to the heart.

The blood is collected into individual containers such as blood bags that are pre-charged with an anticoagulant. The containers are depyrogenated and re-checked for endotoxins. Typical anticoagulants include sodium citrate. The containers and apparatus used in connection with the methods of the present invention should be substantially non-metallic. Preferably, all process steps should be carried out in non-metallic containers.

The containers of collected blood are capped off immediately to avoid exposure to environmental endotoxins. The capped containers are then chilled to about 4° C. to limit bacterial growth.

Once the container contents are pooled, the erythrocytes are concentrated by available techniques. Leukocytes are removed by filtration through commercially available leukocyte removal filters.

The within methods are batch processes that are applicable to commercial volumes of concentrated erythrocyte solutions up to about 100L. Larger batch quantities however are also contemplated.

The erythrocytes are contacted with a hypotonic solution by diluting the erythrocytes with a hypotonic dilution buffer Unlike dialysis methods such as those disclosed in PCT Patent Application No. WO 91US/09615, the erythrocytes are directly contacted with the hypotonic solution in accordance with the present invention. This direct contact provides a significant reduction in phospholipid contamination.

The hypotonic dilution buffer solutions should have an osmolality sufficient to render the erythrocyte membranes hemoglobin permeable without significant lysis. The erythrocytes are preferably diluted at a rate that provides for the release of hemoglobin with a minimum of lysis. The objective of the dilution is to cause the erythrocytes to leak hemoglobin while maintaining the integrity of the erythroctye membrane. This is controlled by the rate of dilution.

The dilution rate is chosen so that when contacted with the hypotonic dilution buffer solution the erythrocytes swell to form a spherical shape. This stretches the pores of the cell membrane so that hemoglobin can be removed from (i.e., leak from) the erythrocytes without disrupting the integrity of the cell membranes. The dilution rate is selected so that the removal of hemoglobin from the erythrocytes occurs with substantially no release of stromal phospholipids from the erythrocytes cell membranes. This represents applicants' definition of the removal of hemoglobin from erythrocytes without significant lysis.

A dilution rate of between about 0.05 to about 0.20 volume percent per minute of the concentrated erythrocytes is suitable for use with the present invention. A dilution rate of 0.10 volume percent per minute of the concentrated erythrocytes is preferred. The dilution is performed with gentle, relatively constant mixing at about 10° C. to about 30° C., preferably room temperature. The dilution can be performed in a single step, or in multiple steps utilizing buffers of varying osmolalities.

Suitable hypotonic dilution buffers contain one or more physiological salts and have a pH greater than about 7.0. A pH between about 7.3 and about 8.0 is preferred. Suitable physiological salts include KCl, NaCl, $KH_2PO_4$, $K_2HPO_4$, $NaH_2PO_4$, $Na_2HPO_4$, $NaHCO_3$ and mixtures thereof.

The suitable hypotonic dilution buffers have an osmolality between about 100 and about 350 milliosmoles per kg. The buffers preferably have an osmolality between about 120 and about 200 milliosmoles/kg, and more preferably between about 120 and about 150 milliosmoles/kg. Examples of suitable buffers include a buffer of 80 mM NaCl, 1.8 mM KCl, 1.33 mM $KH_2PO_4$ and 5.33 mM $K_2HPO_4$, pH 7.4±0.1; a buffer of 60 mM NaCl, 1.35 mM KCl, 1 mM $KH_2PO_4$ and 3.99 mM $K_2HPO_4$, pH 7.4±0.1; a buffer of 70 mM NaCl, 20 mM $NaHCO_3$, 4 mM $KH_2PO_4$ and 2.6 mM $K_2HPO_4$, pH 7.4±0.1; and a buffer of 65 mM NaCl, 1 mM $KH_2PO_4$ and 4 mM $K_2HPO_4$, pH 7.4±0.1. The hypotonic dilution buffers are also preferably substantially free of non-physiological salts.

The erythrocytes are diluted until a hypotonic solution containing erythrocytes having hemoglobin permeable cell membranes is obtained. Dilution is continued until the erythrocyte-containing solution has a hemoglobin concentration between about 2 and about 10 weight percent. A hemoglobin concentration between about 4 and about 6 weight percent is preferred. This requires between about 2 and about 20 erythrocyte volumes of dilution buffer. Between about 5 and about 7.5 erythrocyte volumes of dilution buffer are preferred.

The hypotonic solution containing erythrocytes is then microfiltered so that hemoglobin is separated from the erythrocytes. This is performed utilizing a pyrogen-free hollow fiber cartridge recirculating microfiltration device. The membrane systems of devices suitable for use in the present invention have pore sizes between about 0.1 and about 1.0 microns. The lumen of the microfiltration devices preferably have an inside diameter between about 0.5 and 1.0 mm. The lumen are preferably prepared from hydrophilic materials such as hydrophilic polysulfones, mixed cellulose esters, and the like. Lumen ID's up to about 2.0 mm are contemplated, and ID's greater than or equal to about 0.6 mm are preferred. A pore size of about 0.22 microns is preferred. The membrane device should have a ratio of recirculation volume to membrane surface area between about 10 and about 100L/m². Ratios between about 18 and about 48L/m² are preferred.

The membrane systems should be pre-treated to ensure depyrogenation and proper pH utilizing standard depyrogenation procedures. These procedures include treatment with NaOH and voluminous washings with pyrogen-free water to bring the pH to between about 6.5 and about 8.0.

Hollow fiber cartridge microfiltration devices typically recirculate the volume of sample as microfiltrate is removed. In the present invention, the rate of microfiltrate removal is preferably kept constant at between about 0.01 and about 0.10 sample volumes per minute. A microfiltrate rate of about 0.025 sample volumes per minute is preferred. The inlet pressure of the filtration device should not exceed 25 psi, and is preferably less than about 15 psi.

As the microfiltrate is removed at a constant rate, the recirculating volume of the hypotonic solution containing erythrocytes is maintained constant. The recirculating volume is preferably maintained constant by adding the hypotonic dilution buffer, more preferably at about the rate of microfiltrate removal. The microfiltering process step should be discontinued before the microfiltrate volume significantly exceeds the recirculating sample volume. Preferably, the microfiltrate volume will not exceed about 1.2 times the recirculating sample volume. This will prevent contamination of the microfiltrate with phospholipids, non-heme proteins and polypeptides. The resulting hypotonic hemoglobin microfiltrate solution contains less than about 0.15 weight percent phospholipids. The solution is substantially free of non-heme proteins and polypeptides. About a 50 percent yield of the total hemoglobin content of the erythrocyte solution will be obtained. This translates to a hemoglobin concentration in the microfiltrate solution between about one and about five percent.

The hemoglobin-containing microfiltrate solution has utility in its own right as a hemoglobin product suitable for any of the commercial uses of an extracted hemoglobin. The microfiltrate solution may be utilized without further purification in less critical end-use applications. The hemoglobin microfiltrate solution is particularly suitable as an intermediate in the manufacture of hemoglobin-based blood substitutes for either human or veterinary end use applications. The microfiltrate solution may be optionally concentrated, however, preferred embodiments of the inventive process require no further concentration or buffer exchange.

After this microfiltering step, a 0.22 micron microfiltration may be optionally employed in the same manner as the above-described microfiltering step. An ultrafiltration step using a 100,000 dalton molecular weight cut off may also optionally be employed at this time. A typical device for effecting the ultrafiltration step is a Filtron Centrasette with Filtron Omega membrane cassettes. However, other known devices may be used. The ultrafiltration step is essentially conventional and should be performed utilizing aseptic techniques including depyrogenation steps that are well-known.

The hemoglobin-containing microfiltrate solution may then be purified of residual DNA and phospholipids and contaminating endotoxins by prior art methods. More preferably, however, the microfiltrate solution is purified by the anion exchange process steps of the present invention. The hemoglobin-containing microfiltrate solution may also be utilized without purification as an intermediate in the production of hemoglobin-based blood substitutes. The blood substitutes can then be purified of residual phospholipids and endotoxin contaminants by prior art methods or by the anion exchange process step. The hemoglobin microfiltrate may be stored for up to 12 months at a temperature less than about 8° C. before being purified of DNA, endotoxins and phospholipids.

The anion exchange process of the present invention removes any DNA, phospholipids and endotoxins from hemoglobin-containing solutions having an osmolality between about 100 and about 250 milliosmoles/kg. The solution should have a pH greater than about 7.0. The hemoglobin concentration should be between about 1 and about 10 weight percent, and more preferably between about 1 and about 5 weight percent.

Any hypotonic hemoglobin-containing solution meeting the above requirements can be purified by the anion exchange process. However, the preferred hemoglobin solution meeting the above requirements is the above-described hypotonic hemoglobin microfiltrate solution. The hypotonic hemoglobin microfiltrate solution can be used with the anion exchange process without having to first concentrate or dialyze the microfiltrate. This is particularly advantageous because such steps are economically inefficient and allow the opportunity for endotoxin contamination. The hemoglobin, however, must first be separated from the erythrocytes with a hypotonic buffer having the osmolality required by the anion exchange process.

The hemoglobin solutions preferably contain one or more physiological salts. The preferred physiological salts are selected from KCl, NaCl, $K_2HPO_4$, $KH_2PO_4$, $Na_2HPO_4$, $NaH_2PO_4$ and $NaHCO_3$. More preferably, the solutions are substantially free of non-physiological salts. The hemoglobin solutions have an osmolality between about 120 and about 200 milliosmoles/kg, and more preferably between about 130 and about 168 milliosmoles/kg. Examples of suitable buffers include 20–50 mM pH 8.0 phosphate buffer; a buffer of 40 mM NaCl, 0.9 mM KCl, 3.35 mM $K^+PO_4^{-3}$ and 15 mM $Na^+\cdot PO_4^{-3}$, pH 8.0±0.2; and 65 mM NaCl, 1 mM $KH_2PO_4$, 4 mM $K_2HPO_4$ pH 7.4±0.1. The above-described hypotonic dilution buffers can also be used to prepare buffered hemoglobin solutions.

When the hemoglobin-containing solutions to be purified by the anion exchange process are not within the required osmolality range, the solution osmolality should be adjusted to the required osmolality. The hemoglobin concentration should be adjusted to between about one and about ten weight percent, if not within this range. Precautions should be observed to prevent endotoxin contamination. The solution osmolality and hemoglobin concentration of the microfiltrate can be adjusted by known methods, such as dialysis or dilution.

The anion exchange process preferably chromatographically treats hemoglobin solutions with an anion exchange resin in a liquid chromatography column. A clean, sanitized anion exchange resin is used, capable of binding DNA, phospholipids and endotoxins, but not hemoglobin, at the pH and osmolality of the hemoglobin solution. Any DNA, phospholipids or endotoxins present will bind to the anion exchange resin, with the hemoglobin remaining in solution.

The chromatographic treating of the hemoglobin solutions is more preferably performed by conventional liquid chromatography techniques. Techniques of High Performance Liquid Chromatography (HPLC) are also suitable, but not necessary. Such techniques are not critical to the removal of DNA, endotoxins and phospholipids from the hemoglobin solutions. Conventional liquid chromatography is preferred, because it is more readily adapted to large-scale commercial production techniques than HPLC. A significant economic advantage is also obtained by a reduction in the cost of equipment, process time and risk of endotoxin contamination.

Suitable anion exchange chromatography resins are capable of binding DNA, phospholipids and endotoxins, but not hemoglobin, at osmolalities between about 100 and about 250 milliosmoles/kg, and a pH greater than about 7.0. These resins can be readily identified by evaluation with standardized hemoglobin solutions having the required pH and osmolality. The hemoglobin solution should have a known hemoglobin concentration as well as a known endotoxin and phospholipid concentration. The endotoxin should be a commercially available endotoxin standard. The phospholipids should be a mixture of phosphatidyl-inositol, phosphatidyl-serine, phosphatidyl-choline, sphingomyeline and phosphatidyl-ethanolamine.

Candidate resins should remove greater than 80 percent, preferably greater than 95 percent, of the endotoxins and phospholipids from the standardized solution. The resins should retain less than 20 percent, and preferably less than 10 percent of the hemoglobin in the solution. Typically, the resin is evaluated by packing a 10 mL column with the resin. The packed column is equilibrated with a buffer having the osmolality of the standardized hemoglobin solution. Once equilibrated, a quantity of the standardized solution is injected onto the column providing about 150 to about 350 mg hemoglobin per mL of resin. The column is then eluted with an isocratic flow of the equilibration buffer until the hemoglobin fraction is collected. The hemoglobin, endotoxin and phospholipid concentrations of the hemoglobin fraction are then analyzed by conventional means to evaluate the resin. Typically, endotoxin levels are analyzed by LAL assay, such as the gel clot assay or the kinetic turbidometric assay, whichever is appropriate.

Anion exchange chromatography resins suitable for use in the present invention are typically polar materials coated on suitable supports such as silica or polymers. Strongly polar anion exchange resins work equally well with silica or polymers. The silica may be either neutral or hydrophobic. Weakly polar anion exchange resins require the use of either a neutral or hydrophobic silica matrix.

As is well understood by those of ordinary skill in the art, quaternary amine type chromatography resins exhibit strongly polar anion exchange properties. A number of tetramethylamine, or quaternary methyl amine, anion exchange resins are commercially available, coated onto a variety of support matrices. Suitable commercially available strongly polar resins include QMA-SPHEROSIL ® (M or LS), a quaternary methyl amine resin coated onto a hydrophobic silica base. QMA-SPHEROSIL ® is manufactured by IBF of Garenne, France, for Sepracor of Marlborough, Mass. The preferred QMA-SPHEROSIL ® is QMA-SPHEROSIL LS ®. Another suitable strongly polar resin manufactured by IBF is QA-TRISACRYL ®, a quaternary amine resin coated onto a polymer base. QMA-ACCELL PLUS ®, a quaternary methyl amine coated onto a neutral silica base, is also suitable. This resin is manufactured by the Waters Division of Millipore of Milford, Mass. TMAE ®, a tetramethyl amino ethyl resin coated onto a polyacrylamide polymer matrix can also be used. This resin is manufactured by EM-Separations of Gibbstown, N.J.

An example of weakly polar resins coated onto a silica matrix support are the polyethyleneiminesilanes (PEI) covalently bonded to silica gel. A particularly preferred commercially available resin of this type is WP PEI ® (NH) a wide pore polyethyleneiminesilane bonded to silica gel. This resin is manufactured by JT Baker, Inc. of Phillipsburg, N.J. FMC of Pine Brook, N.J., also manufactures a PEI resin-coated silica gel suitable for use with the present invention.

The chromatography columns should have an axial flow or radial flow design and a diameter between about 1.6 cm and about 1000 cm. The column length should be between about 5 cm and about 1000 cm. Such columns will typically hold between about 1 mL and about 785L of anion exchange chromatography resins. Larger columns or column combinations are contemplated.

Typically, the anion exchange resin is packed in the column and equilibrated by conventional means. A buffer within the same pH and osmolality range as the hemoglobin solution is used. The hemoglobin solution is then passed through the column at a rate of 0.1 to 0.5 column volumes a minute. The chromatography equipment, anion exchange resin, equilibration buffer and elution buffer should be depyrogenated utilizing standard procedures.

The temperature range for the anion exchange process is between about 3° to about 8° C. Fractions containing hemoglobin are collected, while DNA, endotoxins and phospholipids bind to the anion exchange resin. The phospholipids removed by the anion exchange method include phosphatidyl-inositol, phosphatidyl-serine, phosphatidyl-choline, sphingo-myeline and phosphatidyl-ethanolamine. The elution of the hemoglobin fraction is detected by UV absorbance at 280 nm. Hemoglobin fraction collection may be achieved through simple time elution profiles. The collected hemoglobin fractions may be optionally filtered through a Millipore VIRESOLVE ® 70 kilodalton membrane to remove any viral contaminants.

The collected hemoglobin fractions can then be pooled to provide a solution having a hemoglobin concentration between about and about 10 weight percent. If necessary, the fractions can be concentrated and dialyzed to adjust the hemoglobin concentration and to remove any pharmaceutically unacceptable salts. For this reason, the hypotonic dilution buffer is preferably substantially free of non-physiological salts, to eliminate the need for this dialysis step.

Following the collection of the hemoglobin fractions, the chromatographic column should be washed to remove the materials that have bound to the column. The column can then be prepared for another loading of hemoglobin solution to be purified. Typically, the column is washed in a two-step cleaning process. The column is washed with 4 to 10 column volumes of either a 5% solution of acetic acid in methanol or a 70% solution of isopropyl alcohol in 0.5M NaCl. The isopropyl alcohol wash is preferred. The wash is either proceeded or followed by 5 to 10 column volumes of 2 to 3M NaCl in either a 5% acetic acid solution or 10 mM sodium phosphate at a pH between 7.0 and 7.5. The column is then re-equilibrated as described above and the process can then be repeated for another hemoglobin solution requiring purification.

The pooled fractions can be characterized as a solution of hemoglobin in a physiologically acceptable carrier, substantially free of DNA, endotoxins, phospholipids and non-heme proteins and polypeptides. This material has utility in its own right as a hemoglobin product, and as an intermediate product in the production of hemoglobin-based blood substitutes.

The hemoglobin solution may be used immediately or it may be stored for periods as long as 12 months at a temperature less than 8° C. At this temperature, hemoglobin solutions have shown no product degradation or substantial increase in the methemoglobin level. Methemoglobin formation can be retarded by conventional means upon addition to the hemoglobin solutions of from about 5 to about 30 mM cysteine.HCl, from about 2 to about 100 mM sodium dithionate, from about 0.5 to about 1% manitol, from about 0.2 to about 10 mM alpha tocopherol or from about 1 to about 5% glucose.

The hemoglobin microfiltrate, when purified by anion exchange, typically has the characteristics listed in Table I:

TABLE I

| Hemoglobin g/dL | 1-10% |
| --- | --- |
| Oxyhemoglobin | $\geq 95\%$ |
| Carboxyhemoglobin | $\leq 5\%$ |
| Methemoglobin | $< 3\%$ |
| pH | 7.3-8.2 |
| Endotoxin | $< 1$ EU/ml |
| Molecular Weight | 62,000-65,000 daltons |
| Phospholipids | Non-Detectable |
| $P_{50}$ | 20-30 mm Hg @ pH 7.3-7.5 |
| CN-Hemoglobin | Non-Detectable |

The endotoxin level of the eluted hemoglobin solution is determined by a gel clot or kinetic turbometric LAL assay. The non-heme proteins and polypeptides are determined by isoelectric focusing or SDS-PAGE techniques under reducing and non-reducing conditions. Phospholipids can be measured by HPLC Lipid Assay.

Hemoglobin-containing solutions suitable for purification via the anion exchange process also include prior art hemoglobin products and blood substitutes. Hemoglobin products produced by prior art methods are defined as hemoglobin solutions prepared by the separation of hemoglobin from erythrocytes. Hemoglobin solutions produced from recombinant organisms are also included within this definition. For example, the stroma-free hemoglobin solution prepared by Rabiner et al., J. Exp. Med., 126, 1127 (1967) can be purified by the anion exchange process. Likewise, the stroma-free hemoglobin solutions prepared by DeVenuto et al., J. Lab. Clin. Med., 89, 509 (1977) can also be purified by this process.

Blood substitutes that can be purified by the anion exchange process include inter- and/or intra-molecularly cross-linked polymerized hemoglobins. Such compounds are disclosed by U.S. Pat. Nos. 4,001,200, 4,001,401, 4,053,590 and 4,336,248 to Bonsen et al. and U.S. Pat. No. 5,084,558 to Rausch et al. The process can also purify the hemoglobins disclosed by U.S. Pat. Nos. 4,777,244 to Bonhard, 4,529,719 to Tye and 4,584,130 to Bucci. The process can also purify non-polymerized inter- and/or intra-molecularly crosslinked hemoglobins.

The polymer conjugated hemoglobins disclosed by U.S. Pat. Nos. 4,412,989 to Iwashita et al. and 4,900,780 to Cerny can also be purified by the anion exchange process. The polymer conjugated hemoglobins can be polymerized or nonpolymerized and inter- and/or intra-molecularly crosslinked. This process can also be used to purify the polyalkylene oxide conjugated hemoglobins disclosed by U.S. Pat. No. 4,670,417 to Iwaski et al. Such hemoglobins are also disclosed by copending and commonly owned U.S. patent application Ser. Nos. 400,553 and 616,129 filed by Nho et al. The disclosures of both applications, filed on Nov. 22, 1989 and Nov. 20, 1990, respectively, are hereby incorporated herein by reference thereto. The polyalkylene oxide hemoglobin conjugates include conjugates of polyethylene glycol and polypropylene glycol and copolymers thereof. Any hemoglobin product or blood substitute that forms a stable buffer solution at the pH and osmolality required, can be purified by the anion exchange process.

Preferred processes embody both the hemoglobin separation and purification methods of the present invention. For example, ten liters of packed human or bovine red cells are provided. The cells have a hemoglobin concentration of 5 percent and an endotoxin level less than 1.0 EU/mL. The cells are introduced at room temperature into a pyrogen-free non-metallic reactor having impeller blades positioned to effect gentle, constant mixing. Agitation is started, and a first sterile, pyrogen-free hypotonic solution of 80 mM NaCl, 1.8 mM KCl and 6.7 mM R+$PO_4^{-3}$, pH 7.5 is added to the reactor. The hypotonic solution is added at a rate of 0.10 volume percent per minute of the packed red cell volume. The resulting diluted bRBC solution is further diluted with an equal volume of a second hypotonic buffer containing 60 mM NaCl, 1.35 mM KCl, 1 mM $KH_2PO_4$ and 3.99 mM $K_2HPO_4$, pH 7.3-7.5. The solution is diluted at a controlled rate of $0.05 \pm 0.005$ diluted RBC volumes per minute. A second dilution with the first hypotonic solution is then performed by adding an amount equal to about one to one and one-half volumes of the second hypotonic buffer at a rate equal to the controlled rate set forth above, of about $0.05 \pm 0.005$ diluted RBC volumes per minute. Mixing continues for approximately 60 minutes until a buffer suspension of erythrocytes is obtained having a hemoglobin concentration between 4 and 6 weight percent.

The erythrocyte suspension is then microfiltered with a pyrogen-free hollow fiber cartridge recirculating membrane filtration device. Precautions are taken to avoid endotoxin contamination. A typical apparatus is a Microgon KROSFLO II® Microfiltration Module with a membrane system having a lumen ID greater than or equal to 0.6 mm and a pore size of about 0.22 microns. The ratio of recirculation volume to membrane surface area is between about 18 and $36 L/m^2$. The erythrocyte suspension is recirculated at an inlet pressure less than 15 psi with a microfiltrate removal rate of about 0.025 sample volumes per minute. As the microfiltrate is removed, the recirculation volume is maintained at the same rate by addition of the hypotonic solution. Recirculation continues until the microfiltrate volume is about equal to the sample volume. The hemoglobin concentration in the microfiltrate is then between about 1 and about 5 weight percent.

A volume of microfiltrate equal to about 0.5 kg of isolated hemoglobin is then injected onto a 11 cm long 18 cm diameter liquid chromatography column. The column is packed with 2.8L of WP PEI® (JT Baker) anion exchange resin equilibrated with the hypotonic solution. QMA-Spherosil LS® may also be used. The microfiltrate is injected at a rate of 0.35L a minute. Elution of the hemoglobin is detected with a UV detector, at which point collection of the effluent is initiated. Collection continues until the effluent peak has been reduced to less than 5 percent of peak amplitude or less than 0.1% hemoglobin in the column effluent.

The combined procedures produce hemoglobin fractions that, when pooled, typically have a hemoglobin concentration of from about 1.0 to about 2.3 g/dL. The pooled fractions typically have an endotoxin level of less than 0.5 EU/mL as measured by gel clot or kinetic turbidometric LAL assay. The level of non-heme proteins and polypeptides less than 5% mg/mL as determined by isoelectric focusing and SDS-PAGE. The phospholipid level is non-detectable by HPLC lipid assay. The pooled fractions are then stored at $-20°$ C.

for future use, or 2°-8° C. for immediate further processing.

The purification steps are particularly versatile because the same solution can also be utilized to purify prior art hemoglobin products and blood substitutes.

The following non-limiting examples set forth hereinbelow illustrate certain aspects of the invention. These examples are not meant in any way to restrict the effective scope of the invention. All parts and percentages are by weight unless otherwise noted, and all temperatures are in degrees Celsius.

EXAMPLES

Example I: Isolation of Bovine Hemoglobin from Bovine Red Blood Cells

Concentrated bovine red blood cells (bRBC's) were obtained from California Biological and Protein Corporation, Inc. (Huntington Beach, Calif.). The concentrated bRBC's were packed to greater than 90% and had a hemoglobin concentration within the range of 30-35%. The concentrated bRBC's were processed within 24 hours of the initial aseptic bleed and shipped on ice. All processing steps were done at room temperature.

The concentrated bRBC's were pre-filtered through a 25 micron Millipore Polygard-CR cartridge into a polyethylene container. The filtered bRBC's were then diluted under continuous mixing with a quantity of the following hypotonic buffer:

| HYPOTONIC BUFFER A | |
|---|---|
| NaCl | 80 mM |
| KCl | 1.8 mM |
| $K_2HPO_4$ | 1.33 mM |
| $KH_2PO_4$ | 5.33 mM |
| pH | 7.3-7.5 |

The quantity of Hypotonic Buffer A was equivalent to five times the volume of the packed bRBC's. The dilution rate was controlled at 0.1±0.01 bRBC volumes per minute.

The hemoglobin was then extracted from the bRBC solution by recirculation through a 0.22 micron hollow fiber cartridge (Microgon, 0.6 mm lumen ID) under controlled conditions. The ratio of bRBC solution volume to membrane surface area was 15 to 45L/$m^2$. The inlet pressure was less than 15 psig. The filtrate rate was 0.025±0.003 diluted-bRBC volumes per minute. The recirculating bRBC solution was maintained at a constant volume during the extraction process by the addition of Hypotonic Buffer A at the filtrate rate. This was continued until the volume of filtrate containing the extracted bovine hemoglobin was up to 1.2 times the recirculating bRBC solution volume. The extracted bovine hemoglobin was subsequently 0.22 micron filtered into sterile bags for storage.

The solution containing the extracted bovine hemoglobin had a concentration between 1.5 to 2.5% hemoglobin and a methemoglobin concentration of less than 1%.

Example II: Delipidation of Isolated Bovine Hemoglobin using Anion Exchange Chromatography The isolated bovine hemoglobin of Example I was dialyzed into 50 mM sodium phosphate, pH 7.9-8.1. The solution was adjusted to a bovine hemoglobin concentration of between 2 and 8% using the dialysis buffer. The resulting bovine hemoglobin solution was loaded onto a WP-PEI ® (JT Baker) column previously equilibrated in the dialysis buffer. The load flow rate was between 0.1 and 0.3 column volumes per minute. The amount of bovine hemoglobin loaded was based on a resin capacity of 200 to 250 mg bovine hemoglobin per mL resin. The column flow-through containing the bovine hemoglobin was collected and subsequently analyzed for its phospholipid content by HPLC lipid assay. No phospholipids were detected in the post-PEI bovine hemoglobin. The recovery of bovine hemoglobin in the column flow-through was calculated to be greater than 90%. No increase in endotoxin content was observed.

Example III: Delipidation of Isolated Bovine Hemoglobin

The isolated bovine hemoglobin of Example I was diluted with an equal volume of 30 mM sodium phosphate, pH 7.9-8.1. The resulting solution was loaded onto a WP-PEI ® column equilibrated in the 30 mM sodium phosphate buffer at a load flow rate of 0.3 column volumes per minute. The amount of loaded bovine hemoglobin was based on a resin capacity of 200 to 250 mg bovine hemoglobin per mL resin. The column flow-through was collected and analyzed for phospholipid content. No phospholipids were detected. The calculated recovery of bovine hemoglobin in the column flow-through was greater than 90%. No increase in endotoxin content was observed.

Example IV Delipidation of Isolated Bovine Hemoglobin

The isolated bovine hemoglobin of Example I was diluted as in Example III and loaded onto a QMA-SPHEROSIL M ® (IBF/Sepracor) column. The column had been equilibrated in the 30 mM sodium phosphate buffer, and a load flow rate of 0.3 column volumes per minute was used. The amount of loaded bovine hemoglobin was based on a resin capacity of 200 to 250 mg bovine hemoglobin per mL resin. The column flow-through was collected and analyzed for phospholipid content. No phospholipids were detected. The calculated recovery of bovine hemoglobin in the column flow-through was greater than 90% and no increase in endotoxin content was observed.

Example V: Delipidation of Isolatated Bovine Hemoglobin

The isolated bovine hemoglobin of Example I was loaded onto a WP-PEI ® column previously equilibrated in Hypotonic Buffer A. A load flow rate of 0.3 column volumes per minute was used, and the column was loaded at 200 to 250 mg bovine hemoglobin per mL resin. The column flow-through was collected and analyzed for phospholipid content. No phospholipids were detected. Recovery of bovine hemoglobin in the column flow-through was greater than 90% and no increase in endotoxin content was observed.

VI: Delipidation of Isolated Bovine Hemoglobin

The isolated bovine hemoglobin of Example I was loaded onto a QMA-SPHEROSIL M ® column equilibrated in Hypotonic Buffer A. A load flow rate of 0.3 column volumes per minute was used and the column was loaded at 200 to 250 mg bovine hemoglobin per mL resin. The column flow-through was collected and analyzed for phospholipid content. No phospholipids were detected. Recovery of the bovine hemoglobin in the column flow-through was calculated to be greater than 90% and no increase in endotoxin content was observed.

Example VII: Isolation of Bovine Hemoglobin from Bovine Red Blood Cells using a Two-Step Dilution Process Concentrated bRBC's were obtained as described in Example I. The received packed bRBC's were prefiltered as described in Example I and then diluted, under continous mixing, with an equal volume of Hypotonic Buffer A. A controlled dilution rate of 0.1±0.01 bRBC's volumes per minute was used. The resulting diluted bRBC solution was further diluted with an equal volume of the following buffer:

| HYPOTONIC BUFFER B | |
| --- | --- |
| NaCl | 60 mM |
| KCl | 1.35 mM |
| $KH_2PO_4$ | 1 mM |
| $K_2HPO_4$ | 3.99 mM |
| pH | 7.3–7.5 |

The solution was diluted at a controlled dilution rate of 0.05±0.005 diluted RBC volumes per minute. A second dilution with Hypotonic Buffer A was then performed. A quantity of Hypotonic Buffer A equivalent to the volume of Hyptonic Buffer B added was added at a controlled rate of 0.05±0.005 diluted RBC volumes per minute. The final diluted bRBC solution had an osmolarity of 163±5 milliosmoles/kg. The final volume was equivalent to six times the initial volume of the concentration bRBC's. Once the final diluted bRBC solution was obtained, the bovine hemoglobin was extracted as described in Example I.

The bovine hemoglobin recovered by the methods of Examples I and VII is typically between 45 to 60% of the total bovine hemoglobin available in the bRBC's. The isolated bovine hemoglobin has a concentration between 1.5 and 3%, a $P_{50}$ (pH 7.4±0.1) between 20 and 28 mm Hg and an endotoxin level of less than 0.5 EU/mL. The hemoglobin had a methemoglobin concentration of less than 1% and a purity greater than 95% (determined by isoelectric focusing and SDS-PAGE, both reducing and non-reducing). The phospholipid content is less than 0.15% by weight. RBC lysis was monitored by visual examination of the RBC solution through a high powered microscope, by percent purity of the hemoglobin, and by phospholipid content.

Numerous variations and combinations of the features set forth above can be utilized without departing from the present invention as set forth in the claims. Such variations are not regarded as a departure from the spirit and scope of the invention. All such modifications are intended to be included within the scope of the following claims.

We claim:

1. A method for separating hemoglobin from erythrocytes, comprising:
   contacting erythrocytes with a hypotonic buffer solution with relatively constant mixing at a rate sufficient to render the release of hemoglobin from said erythrocytes without significant lysis; and
   separating said hemoglobin from said erythrocytes.

2. The method of claim 1, further comprising the step of washing said erythrocytes with isotonic saline before said contacting step.

3. The method of claim 2, wherein said washing step comprises washing said erythrocytes once with isotonic saline.

4. The method of claim 2, wherein said washing step comprises washing said erythrocytes repeatedly with said isotonic saline until said erythrocytes are substantially free of plasma proteins.

5. The method of claim 1, wherein said erythrocytes are substantially free of leukocytes and reticulocytes.

6. The method of claim 1, wherein said erythrocytes comprise an erythrocyte concentrate in an isotonic solution.

7. The method of claim 6, wherein said erythrocytes are present in said isotonic solution at a concentration of at least 50 g/100 mL.

8. The method of claim 7, wherein said erythrocytes are present in said isotonic solution at a concentration of at least 75 g/100 mL.

9. The method of claim 8, wherein said erythrocytes are present in said isotonic solution at a concentration of at least 95 g/100 mL.

10. The method of claim 1, wherein said hypotonic buffer solution comprises one or more physiological salts.

11. The method of claim 10, wherein said one or more physiological salts are selected from the group consisting of KCl, NaCl, $Na_2HPO_4$, $NaH_2PO_4$, $K_2HPO_4$, $KH_2PO_4$ and $NaHCO_3$.

12. The method of claim 10, wherein said hypotonic buffer solution is substantially free of non-physiological salts.

13. The method of claim 1, wherein said rate is between about 0.05 to about 0.20 volume percent of said erythrocytes per minute.

14. The method of claim 13, wherein said rate is about 0.10 volume percent of said erythrocytes per minute.

15. The method of claim 1, wherein said contacting step comprises contacting said erythrocytes with said hypotonic buffer solution at a temperature between about 10° C. and about 30° C.

16. The method of claim 15, wherein said temperature is room temperature.

17. The method of claim 1, wherein said hypotonic buffer solution has an osmolality of between about 100 and 350 milliosmoles/kg.

18. The method of claim 17, wherein said hypotonic buffer solution has an osmolality of between about 120 and about 200 milliosmoles/kg.

19. The method of claim 18, wherein said hypotonic buffer solution has an osmolality of between about 120 and 150 milliosmoles/kg.

20. The method of claim 1, wherein said separating step comprises microfiltering said erythrocytes so that a hypotonic hemoglobin solution is obtained; and recovering said hypotonic hemoglobin solution.

21. The method of claim 20, wherein said recovering step comprises recovering said hypotonic hemoglobin microfiltrate solution at a constant microfiltrate rate.

22. The method of claim 21, wherein said constant microfiltrate rate is between about 0.01 and about 0.1 sample volumes per minute.

23. The method of claim 22, wherein said constant microfiltrate rate is about 0.025 sample volumes per minute.

24. The method of claim 21, wherein said microfiltering step further comprises maintaining the volume of said hypotonic solution contacting said erythrocytes equal to said microfiltrate rate.

25. The method of claim 21, wherein said hypotonic hemoglobin microfiltrate solution is recovered before the microfiltrate volume exceeds said volume of said solution of hemoglobin-permeable erythrocytes.

26. The method of claim 1, wherein the pH of said hypotonic buffer solution is at least about 7.0.

27. The method of claim 26, wherein said pH is between about 7.3 and about 8.

28. The method of claim 21, further comprising contacting said hypotonic hemoglobin solution with an anion exchange medium which is capable of selectively binding DNA, phospholipids and endotoxins, but not hemoglobin, from hypotonic solutions whereby said DNA, phospholipids and endotoxins bind to said anion exchange medium and are substantially removed from said hypotonic hemoglobin solution.

29. The method of claim 28, wherein said anion exchange medium comprises an anion exchange chromatography resin, and said step of contacting said hypotonic hemoglobin solution with said anion exchange medium comprises chromatographically treating said hypotonic hemoglobin solution with said anion exchange chromatography resin in a liquid chromatography column.

30. The method of claim 29, wherein said anion exchange chromatography resin comprises a quaternary amine coated on a polymeric matrix or a neutral or hydrophobic silica matrix.

31. The method of claim 29, wherein said anion exchange chromatography resin comprises a polyethyleneimine coated on a neutral or hydrophobic silica matrix.

32. The method of claim 1, wherein said erythrocytes comprise mammalian erythrocytes.

33. The method of claim 32, wherein said erythrocytes comprise human erythrocytes.

34. The method of claim 32, wherein said erythrocytes comprise ruminant erythrocytes.

35. The method of claim 34, wherein said ruminant erythrocytes comprise bovine erythrocytes.

36. The method of claim 1, wherein said erythrocytes comprise transgenic erythrocytes.

37. A method for purifying a hemoglobin-containing solution of phospholipids and endotoxins, which method comprises the steps of:
   (a) providing a solution of hemoglobin having a pH greater than about 7.0, and an osmolality between about 100 and about 250 milliosmoles;
   (b) contacting said hemoglobin solution with an anion exchange medium capable of selectively binding DNA, phospholipids and endotoxins, but not hemoglobin, at said pH and osmolality of said hemoglobin solution, so that said DNA, phospholipids and said endotoxins bind to said anion exchange medium and said hemoglobin remains in said solution; and
   (c) recovering said hemoglobin solution.

38. The method of claim 37, wherein said hemoglobin solution comprises one or more physiological salts.

39. The method of claim 38, wherein said one or more physiological salts are selected from the group consisting of KCl, NaCl, $Na_2HPO_4$, $NaH_2PO_4$, $K_2HPO_4$, $KH_2PO_4$ and $NaHCO_3$.

40. The method of claim 38, wherein said hemoglobin solution is substantially free of non-physiological salts.

41. The method of claim 37, wherein said osmolality of said hemoglobin solution is between about 120 and about 200 milliosmoles.

42. The method of claim 41, wherein said osmolality of said hemoglobin solution is between about 130 and about 168 milliosmoles.

43. The method of claim 42, wherein said anion exchange medium comprises an anion exchange chromatography resin, and said step of contacting said hemoglobin solution with an anion exchange medium comprises the step of chromatographically treating said hemoglobin solution with said anion exchange resin in a liquid chromatography column.

44. The method of claim 43, wherein said anion exchange chromatography resin comprises a quaternary amine coated on a polymeric matrix or a neutral or hydrophobic silica or mixed silica-polymeric matrix.

45. The method of claim 43, wherein said anion exchange chromatography resin comprises a polyethyleneimine coated on a neutral or hydrophobic silica matrix.

46. The method of claim 37, wherein said providing of said hemoglobin solution comprises the steps of:
   contacting erythrocytes with a hypotonic buffer solution at a rate sufficient to render the release of hemoglobin from said erythrocyte without significant lysis; and
   separating said hemoglobin from said erythrocytes.

47. The method of claim 37, wherein said hemoglobin comprises mammalian hemoglobin.

48. The method of claim 47, wherein said hemoglobin comprises human hemoglobin.

49. The method of claim 47, wherein said hemoglobin comprises ruminant hemoglobin.

50. The method of claim 49, wherein said ruminant hemoglobin comprises bovine hemoglobin.

51. The method of claim 37, wherein said hemoglobin comprises a hemoglobin produced by recombinant methods.

52. The method of claim 37, wherein said solution of hemoglobin comprises a hemoglobin-based blood substitute.

53. The method of claim 52, wherein said hemoglobin-based blood substitute comprises an intermolecularly cross-linked polymerized hemoglobin.

54. The method of claim 53, wherein said intermolecularly cross-linked polymerized hemoglobin is intramolecularly cross-linked.

55. The method of claim 52, wherein said hemoglobin-based blood substitute comprises intramolecularly cross-linked non-polymerized hemoglobin.

56. The method of claim 52, wherein said hemoglobin-based blood substitute comprises intermolecularly cross-linked non-polymerized hemoglobin.

57. The method of claim 52, wherein said hemoglobin-based blood substitute comprises polymer conjugated hemoglobin.

58. The method of claim 57, wherein said polymer conjugated to said hemoglobin comprises a polyalkylene oxide.

59. The method of claim 58, wherein said polyalkylene oxide is selected from the group consisting of polyethylene glycol, polypropylene glycol and block copolymers thereof.

60. The method of claim 57, wherein said polymer-conjugated hemoglobin is polymerized by intermolecular cross-linking.

61. The method of claim 60, wherein said polymerized polymer conjugated hemoglobin is intramolecularly cross-linked.

62. The method of claim 57, wherein said polymer conjugated hemoglobin is intermolecularly cross-linked without polymerization.

63. The method of claim 62, wherein said hemoglobin is intramolecularly cross-linked.

64. The method of claim 57, wherein said polymer conjugated hemoglobin is intramolecularly cross-linked without polymerization.

* * * * *

UNITED STATES PATENT AND TRADEMARK OFFICE
CERTIFICATE OF CORRECTION

PATENT NO. : 5,264,555

DATED : November 23, 1993

INVENTOR(S) : Shorr et al

It is certified that error appears in the above-indentified patent and that said Letters Patent is hereby corrected as shown below:

Column 5, line 37, after "dilution buffer" insert --.--.

Column 10, line 30, "between about and about 10 weight percent" should read --between about 1 and about 10 weight percent--.

Column 12, line 11, "6.7 mM $R^+PO_4^{-3}$" should read --6.7 mM $K^+PO_4^{-3}$--.

Signed and Sealed this

Third Day of May, 1994

Attest:

BRUCE LEHMAN

Attesting Officer

Commissioner of Patents and Trademarks